United States Patent
Gu et al.

(10) Patent No.: US 11,752,098 B2
(45) Date of Patent: Sep. 12, 2023

(54) CORE-SHELL MICRONEEDLE PATCH FOR $H_2O_2$ AND PH CASCADE-TRIGGERED INSULIN DELIVERY

(71) Applicant: NORTH CAROLINA STATE UNIVERSITY, Raleigh, NC (US)

(72) Inventors: Zhen Gu, Los Angeles, CA (US); Jinqiang Wang, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 313 days.

(21) Appl. No.: 16/755,191

(22) PCT Filed: Oct. 10, 2018

(86) PCT No.: PCT/US2018/055170
§ 371 (c)(1),
(2) Date: Apr. 10, 2020

(87) PCT Pub. No.: WO2019/075029
PCT Pub. Date: Apr. 18, 2019

(65) Prior Publication Data
US 2021/0186865 A1 Jun. 24, 2021

Related U.S. Application Data

(60) Provisional application No. 62/570,498, filed on Oct. 10, 2017.

(51) Int. Cl.
*A61K 9/00* (2006.01)
*A61P 3/10* (2006.01)
*A61K 9/107* (2006.01)

(52) U.S. Cl.
CPC .......... *A61K 9/0021* (2013.01); *A61K 9/1075* (2013.01); *A61P 3/10* (2018.01)

(58) Field of Classification Search
None
See application file for complete search history.

(56) References Cited

U.S. PATENT DOCUMENTS

| 6,030,827 A * | 2/2000 | Davis | C12Q 1/004 204/403.12 |
| 10,640,592 B2 * | 5/2020 | Shen | A61K 47/595 |
| 2015/0030641 A1 * | 1/2015 | Anderson | A61K 9/5138 424/94.4 |

FOREIGN PATENT DOCUMENTS

CN 102294212 B 10/2013

OTHER PUBLICATIONS

Li et al. Journal of Nanoscience and Nanotechnology 2016 16:5457-5463 (Year: 2016).*
Zhang et al. Polymer Chemistry 2016 7:1494-1504 (Year: 2016).*
Han et al. Macromolecular Rapid Communications 2013 34:574-580 (Year: 2013).*
Yang et al Soft Matter 2013 9:8589-8599 (Year: 2013).*
Deng et al. ACS Macro Letters 2015 4:220-224 (Year: 2015).*
Morgacheva et al. Russian Journal of Applied Chemistry, 2015 88(4):617-621 (Year: 2015).*
Valo et al. Journal of Controlled Release 2011 156:390-397 (Year: 2011).*
Cao et al. Journal of Drug Delivery Science and Technology 2016 35:1-7 (Year: 2016).*
Seno et al. Materials Science and Engineering C 2016 62:474-479 (Year: 2016).*
A. A. Obaidat, K. Park, Pharmaceut. Res. 1996, 13, 989-995.
A. Matsumoto, R. Yoshida, K. Kataoka, Biomacromolecules 2004, 5, 1038-1045.
B. W. Bequette, Diabetes Technol. Ther. 2005, 7, 28-47.
C. De Duve, P. Baudhuin, Physiol. Rev. 1966, 46, 323-357.
C. M. Hassan, F. J. Doyle, N. A. Peppas, Macromolecules 1997, 30, 6166-6173.
C. M. Wong, K. H. Wong, X. D. Chen, Appl. Microbiol. Biotechnol. 2008, 78, 927-938.
C. R. Gordijo, K. Koulajian, A. J. Shuhendler, L. D. Bonifacio, H. Y. Huang, S. Chiang, G. A. Ozin, A. Giacca, X. Y. Wu, Adv. Funct. Mater. 2011, 21, 73-82.
C. Wang, Chao, et al. Red blood cells for glucose-responsive insulin delivery. Advanced Materials 29.18 (2017): 1606617.
D. H. Chou, M. J. Webber, B. C. Tang, A. B. Lin, L. S. Thapa, D. Deng, J. V. Truong, A. B. Cortinas, R. Langer, D. G. Anderson, Proc. Natl. Acad. Sci. U. S. A. 2015, 112, 2401-2406.
D. R. Owens, B. Zinman, G. B. Bolli, Lancet 2001, 358, 739-746.
D. Scott, A. Fisher, J. Pharmacol. Exp. Ther. 1936, 58, 78-92.
D. Shiino, Y. Murata, A. Kubo, Y. J. Kim, K. Kataoka, Y. Koyama, A. Kikuchi, M. Yokoyama, Y. Sakurai, T. Okano, J. Control. Release 1995, 37, 269-276.
E. Cengiz, J. L. Sherr, S. A. Weinzimer, W. V. Tamborlane, Expert Rev. Med. Devices 2011, 8, 449-458.
F. Balkwill, Eur. J. Cancer 2006, 42, 567-571.
F. Liu, S. C. Song, D. Mix, M. Baudys, S. W. Kim, Bioconjug. Chem. 1997, 8, 664-672.
G. Saravanakumar, J. Kim, W. J. Kim, Advanced Science 2017, 4, 1600124.
G. Springsteen, B. Wang, Tetrahedron 2002, 58, 5291-5300.
I. C. Lee, J.-S. He, M.-T. Tsai, K.-C. Lin, J. Mater. Chem. B 2015, 3, 276-285.
J. C. Yu, C. G. Qian, Y. Q. Zhang, Z. Cui, Y. Zhu, Q. D. Shen, F. S. Ligler, J. B. Buse, Z. Gu, Nano Lett. 2017, 17, 733-739.
J. Yu, Y. Zhang, Y. Ye, R. DiSanto, W. Sun, D. Ranson, F. S. Ligler, J. B. Buse, Z. Gu, Proc. Natl. Acad. Sci. U. S. A. 2015, 112, 8260-8265.
K. Kataoka, H. Miyazaki, M. Bunya, T. Okano, Y. Sakurai, J. Am. Chem. Soc. 1998, 120, 12694-12695.
K. M. Bratlie, R. L. York, M. A. Invernale, R. Langer, D. G. Anderson, Adv. Healthc. Mater. 2012, 1, 267-284.

(Continued)

*Primary Examiner* — Melissa S Mercier
*Assistant Examiner* — Caralynne E Helm
(74) *Attorney, Agent, or Firm* — Meunier Carlin & Curfman LLC

(57) ABSTRACT

Disclosed are compositions and methods for microneedle patches comprising diblock copolymer micelles designed for pH cascade and $H_2O_2$ triggered insulin delivery.

7 Claims, 14 Drawing Sheets

(56) References Cited

OTHER PUBLICATIONS

K. Podual, F. J. Doyle Iii, N. A. Peppas, J. Control. Release 2000, 67, 9-17.
K. Podual, F. J. Doyle, N. A. Peppas, Polymer 2000, 41, 3975-3983.
K. Zhang, X. Y. Wu, J. Control. Release 2002, 80, 169-178.
M. Brownlee, A. Cerami, Diabetes 1983, 32, 499-504.
M. Brownlee, A. Cerami, Science 1979, 206, 1190-1191.
M. Piest, X. Zhang, J. Trinidad, J. F. Engbersen, Soft Matter 2011, 7, 11111-11118.
Matsumoto, T. Kurata, D. Shiino, K. Kataoka, Macromolecules 2004, 37, 1502-1510.
N. A. Peppas, Y. Huang, M. Torres-Lugo, J. H. Ward, J. Zhang, Annu. Rev. Biomed. Eng. 2000, 2, 9-29.
O. Olatunji, D. B. Das, M. J. Garland, L. Belaid, R. F. Donnelly, J. Pharm. Sci. 2013, 102, 1209-1221.
O. Veiseh, B. C. Tang, K. A. Whitehead, D. G. Anderson, R. Langer, Nat. Rev. Drug Discov. 2015, 14, 45-57.
O. Wintersteiner, H. A. Abramson, J. Biol. Chem. 1933, 99, 741-753.
R. Mo, T. Jiang, J. Di, W. Tai, Z. Gu, Chem. Soc. Rev. 2014, 43, 3595-3629.
S. Joel, K. B. Turner, S. Daunert, ACS Chem. Biol. 2014, 9, 1595-1602.
S. P. Davis, B. J. Landis, Z. H. Adams, M. G. Allen, M. R. Prausnitz, J. Biomech. 2004, 37, 1155-1163.
W. A. Broom, C. E. Coulthard, M. R. Gurd, M. E. Sharpe, Br. J. Pharmacol. Chemother. 1946, 1, 225-233.
W. L. A. Brooks, B. S. Sumerlin, Chem. Rev. 2016, 116, 1375-1397.
W. Park, D. Kim, H. C. Kang, Y. H. Bae, K. Na, Biomaterials 2012, 33, 8848-8857.
W. Tai, R. Mo, J. Di, V. Subramanian, X. Gu, J. B. Buse, Z. Gu, Biomacromolecules 2014, 15, 3495-3502.
X. L. Hu, J. C. Yu, C. G. Qian, Y. Lu, A. R. Kahkoska, Z. G. Xie, X. B. Jing, J. B. Buse, Z. Gu, ACS Nano 2017, 11, 613-620.
X. Liu, J. Xiang, D. Zhu, L. Jiang, Z. Zhou, J. Tang, X. Liu, Y. Huang, Y. Shen, Adv. Mater. 2016, 28, 1743-1752.
Y. Dong, W. Wang, O. Veiseh, E. A. Appel, K. Xue, M. J. Webber, B. C. Tang, X.-W. Yang, G. C. Weir, R. Langer, D. G. Anderson, Langmuir 2016, 32, 8743-8747.
Y. Liu, J. Du, M. Yan, M. Y. Lau, J. Hu, H. Han, O. O. Yang, S. Liang, W. Wei, H. Wang, J. Li, X. Zhu, L. Shi, W. Chen, C. Ji, Y. Lu, Nat. Nano. 2013, 8, 187-192.
Y. Ohkubo, H. Kishikawa, E. Araki, T. Miyata, S. Isami, S. Motoyoshi, Y. Kojima, N. Furuyoshi, M. Shichiri, Diabetes Res. Clin. Pract. 1995, 28, 103-117.
Y. Yamamoto, H. Koma, T. Yagami, Neurotoxicology 2015, 49, 86-93.
Z. Gu, A. A. Aimetti, Q. Wang, T. T. Dang, Y. Zhang, O. Veiseh, H. Cheng, R. S. Langer, D. G. Anderson, ACS Nano 2013, 7, 4194-4201.
Z. Gu, T. T. Dang, M. Ma, B. C. Tang, H. Cheng, S. Jiang, Y. Dong, Y. Zhang, D. G. Anderson, ACS Nano 2013, 7, 6758-6766.
J. Q. Wang, W. W. Mao, L. L. Lock, J. B. Tang, M. H. Sui, W. L. Sun, H. G. Cui, D. Xu, Y. Q. Shen, ACS nano 2015, 9, 7195-7206.
International Preliminary Report issued for Application No. PCT/US2018/055170, dated Patentability dated Apr. 23, 2020.
Office Action and Search Report, dated Oct. 24, 2022, received in connection with corresponding CN Patent Application No. 201880078686.2. (and English translation).
Xu, B., et al. "H2O2-Responsive mesoporous silica nanoparticles integrated with microneedle patches for the glucose-monitored transdermal delivery of insulin," Journal of Materials Chemistry B, vol. 5, No. 41, 2017, pp. 8200-8208.

\* cited by examiner

CORE-SHELL MICRONEEDLE PATCH FOR $H_2O_2$ AND PH CASCADE-TRIGGERED INSULIN DELIVERY

This is a national phase application filed under 35 U.S.C. § 371 of PCT International Application No. PCT/US2018/055170, filed on Oct. 10, 2018, entitled "CORE-SHELL MICRONEEDLE PATCH FOR $H_2O_2$ AND PH CASCADE-TRIGGERED INSULIN DELIVERY," which claims the benefit of, U.S. Provisional Application No. 62/570,498, filed Oct. 10, 2017, applications which are incorporated herein by reference in their entireties. This invention was made with government support under Grant No. 1708620 awarded by the National Science Foundation. The government has certain rights in the invention.

This invention was made with government support under Grant No. 1708620 awarded by National Science Foundation. The government has certain rights in the invention.

I. BACKGROUND

Diabetes mellitus is a global disease affecting 422 million people in 2016. It is characterized by a deficit of endogenously-produced insulin and thereafter elevated blood glucose levels (BGLs). Open-loop subcutaneous injection of insulin cannot regulate BGLs tightly and is associated with a risk of severe hypoglycemia. A closed-loop system that can "secret" desirable amounts of insulin in response to hyperglycemia while maintaining basal insulin release kinetics under normoglycemia is urgently needed. Electronic closed-loop devices that have been developed to this end remain challenges regarding algorithm accuracy and sensor reliability. Alternatively, chemically-engineered formulations or devices with the assistance of GOx, phenylboronic acid (PBA) and glucose binding protein (GBP) have attracted increasing attention. For example, GOx catalyzes the oxidation of glucose to gluconic acid in the presence of oxygen and generates hydrogen peroxide ($H_2O_2$). Accordingly, GOx can create a local oxidative and acidic environment triggered by elevated glucose levels to promote the release of insulin pre-loaded in acid-responsive systems. However, the typical pH change-triggered response of materials is often impaired by undesirable delay owing to the relatively slow changes in conformation and morphology of materials and formulations under a physiological condition. In addition, the in vivo release of GOx from medical devices may cause potential toxicity, as well as the concerns over long-term biocompatibility of the $H_2O_2$ generated during oxidation of glucose. Therefore, the ongoing need for the development of new smart insulin delivery systems not hindered by the deficiencies of present systems.

II. SUMMARY

Disclosed are methods and compositions related to microneedle patches for insulin delivery.

In one aspect, disclosed herein are microneedle patches comprising diblock copolymer micelles; wherein the diblock copolymer micelles comprise separately insulin and a glucose responsive enzyme; wherein the microneedles are coated with $H_2O_2$ scavenging enzyme; and wherein the insulin dissociates from the micelle in an acidic and oxidative environment.

Also disclosed herein are microneedle patches of any preceding aspect, wherein the diblock copolymer comprises $mPEG_n$-poly(2-(dimethylamino)ethyl methacrylate (bromoethyl)phenylboronic acid)$_m$ ($MPEG_n$-P(DMAEMA-PBA)$_m$); wherein n can be between 1 and 8,000; and wherein m can be between 1 and 18,000.

In one aspect disclosed herein are microneedle patches of any preceding aspect, wherein the diblock copolymer micelles further comprise poly(vinyl alcohol) (PVA) and/or PVA methacrylate (m-PVA), wherein the PVA and/or m-PVA is incorporated into the micelle via acid-inert ester bonds between the phenylboronic acids of P(DMAEMA-PBA) and PVA or m-PVA.

Also disclosed herein are microneedle patches of any preceding aspect, wherein the glucose responsive enzyme is glucose oxidase and/or wherein the $H_2O_2$ scavenging enzyme comprises catalase In one aspect, disclosed herein are microneedle patches of any preceding aspect, wherein the microneedles comprise a core and micelles are crosslinked to the microneedle core. Also disclosed herein are microneedle patches of any preceding aspect, wherein the diblock copolymer micelles are crosslinked to the microneedle core via non-cleavable covalent bond.

In one aspect, disclosed herein are microneedle patches of any preceding aspect, wherein the H2O2 scavenging enzyme comprises a peroxisome catalase nanogel.

Also disclosed herein are self-regulating insulin delivery systems comprising the microneedle patch of any preceding aspect.

In one aspect, disclosed herein are methods of treating hyperglycemia in a subject comprising administering to the subject the microneedle patch of any preceding aspect. Also disclosed are methods of any preceding aspect, wherein the hyperglycemia is a symptom of diabetes. For example, in one aspect disclosed herein are methods of treating diabetes in a subject comprising administering to the subject a microneedle patch comprising diblock copolymer micelles; wherein the diblock copolymer micelles comprise separately insulin and glucose oxidase; wherein the microneedles are coated with $H_2O_2$ scavenging enzyme; and wherein the insulin dissociates from the micelle in an acidic and oxidative environment.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows a schematic of the glucose-responsive insulin delivery system utilizing $H_2O_2$ and pH cascade-responsive NC-loading MN-array patch. FIG. 1A shows the formation of insulin and GOx NCs and mechanism of glucose-responsive insulin release. FIG. 1B shows a schematic of $H_2O_2$ triggered charge reduction of the polymer. FIG. 1C shows a schematic of the NC-containing core-shell MN-array patch for in vivo insulin delivery. Insulin release is triggered under a hyperglycemic state. FIG. 1D shows a schematic illustration of $H_2O_2$ generation by GOx-NG and elimination by CAT-NG.

Figure 7:
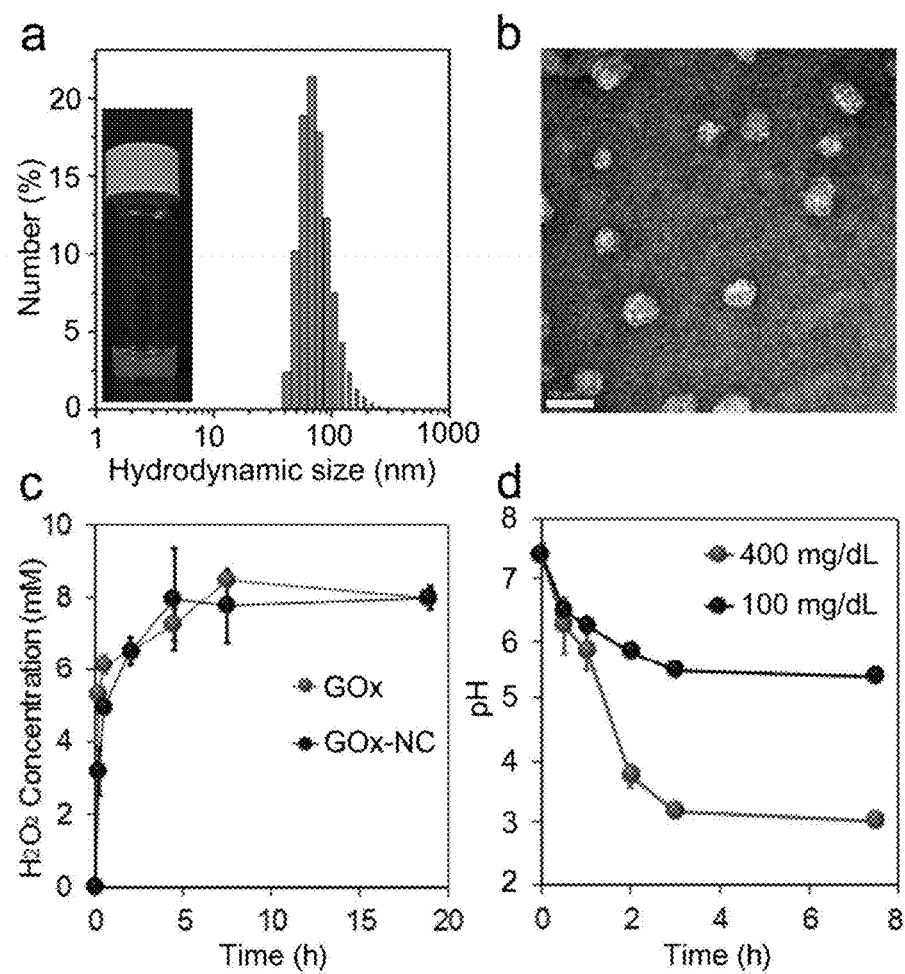

FIG. 7 shows the characterizations of Ins-NC and GOx-NC. (a) Representative image of Ins-NC solution and hydrodynamic size distribution of Ins-NC as determined by DLS. Inset: a representative picture of an Ins-NC solution sample (insulin dose: 1 mg/mL). (b) Representative TEM image of Ins-NC. Scale bar, 100 nm. (c) $H_2O_2$ generation of GOx and GOx-NC in PBS containing glucose (400 mg/dL). (d) The pH change of PBS solution containing different glucose concentrations (100 or 400 mg/dL) in the presence of GOx-NC (0.2 mg/mL GOx-eq. concentration). Data points represent mean±SD (n=3). Error bars indicate SD.

Figure 8:
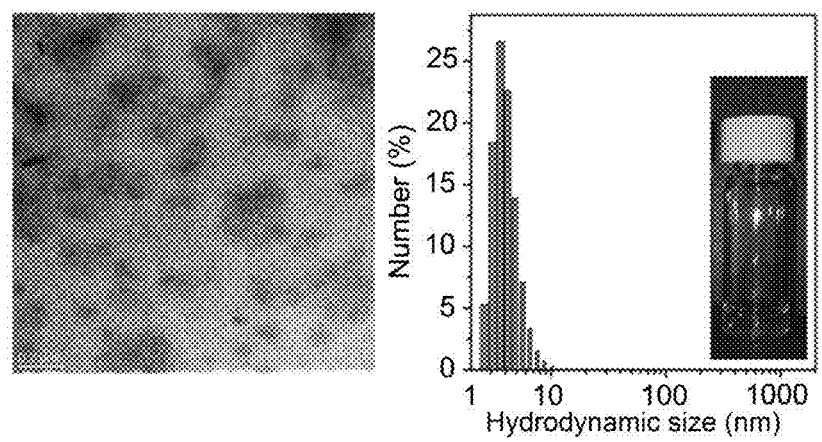

FIG. 8 shows a Representative TEM image and size distribution of Ins-NC after treated by PBS containing glucose (400 mg/dL) in the presence of GOx.

Figure 9:
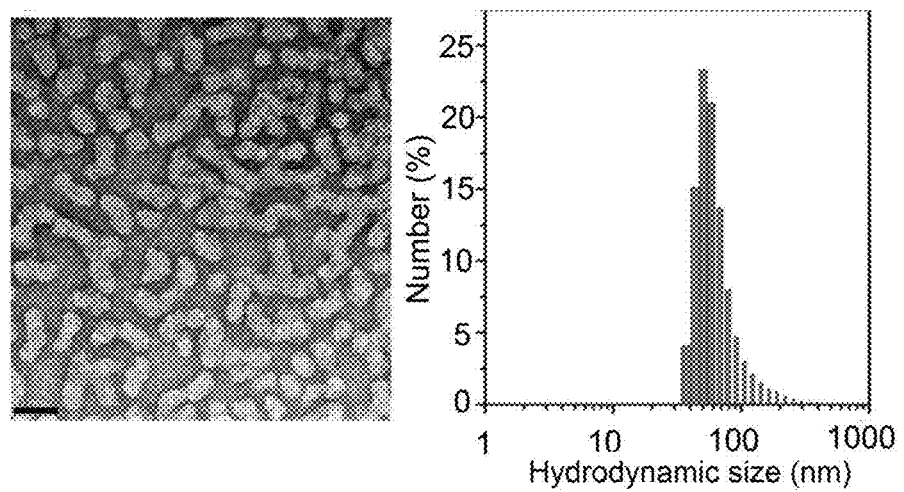

FIG. 9 shows Representative TEM images and size distribution of GOx-NC.

Figure 10:
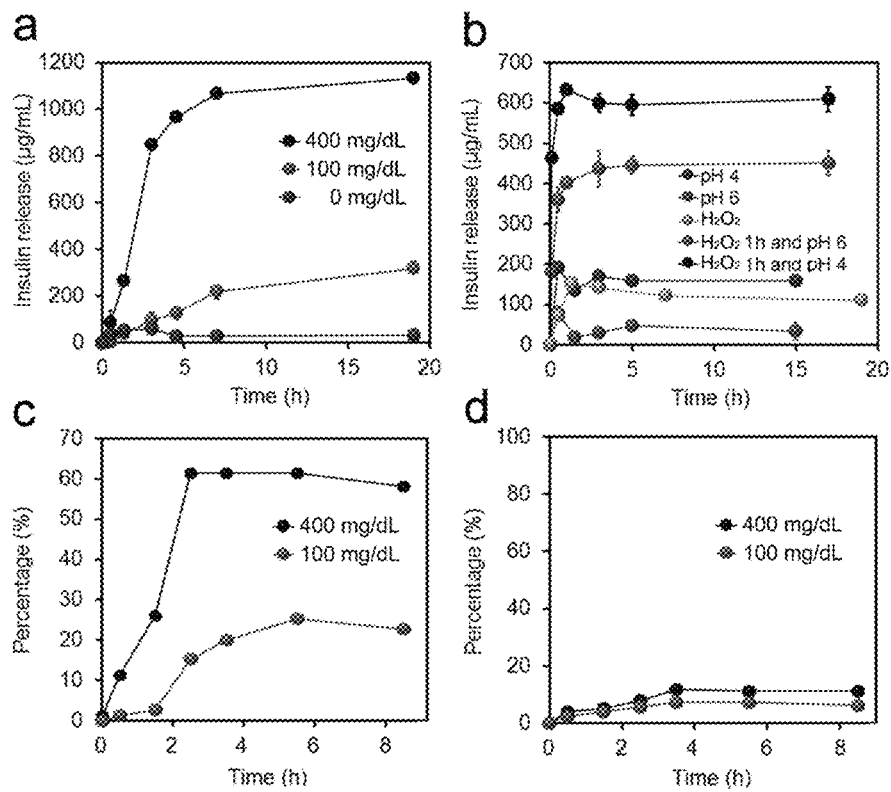

FIG. 10 shows the in vitro characterization of glucose-responsive insulin release. (a) Glucose concentration-dependent insulin release from a complex of insulin in PBS 7.4 in the presence of GOx (0.2 mg/mL). The glucose concentration was set as 0, 100 and 400 mg/dL. (b) pH and $H_2O_2$ cascade-triggered insulin release from Ins-NC. (c) Glucose concentration-dependent insulin release from Ins-NC loaded in PVA gel in PBS 7.4 in the presence of GOx (0.2 mg/mL). (d) Glucose concentration-dependent GOx release from GOx-NC encapsulated in PVA gel in PBS 7.4. Additional GOx (0.2 mg/mL) was added. The glucose concentration was set as 100 and 400 mg/dL. Data points represent mean±SD (n=3). Error bars indicate SD.

Figure 11:
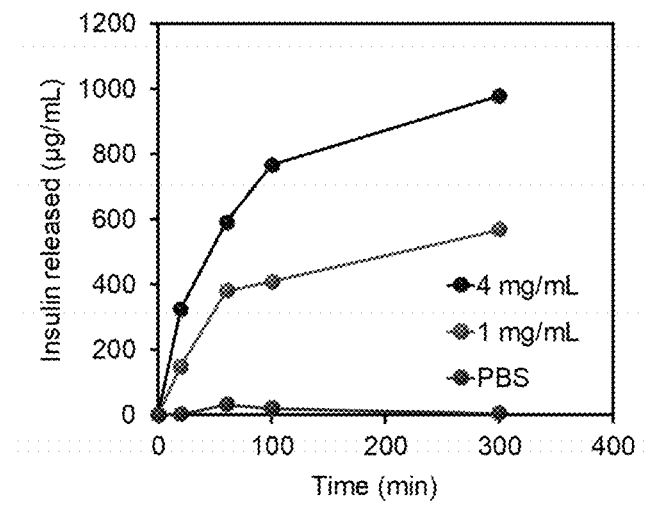

FIG. 11 shows an insulin release profile from complex from insulin and poly(DMAEMA-PBA) in PBS at pH 7.4 in the presence of GOx (0.2 mg/mL) with different glucose concentration (400, 100 and 0 mg/dL).

Figure 12:
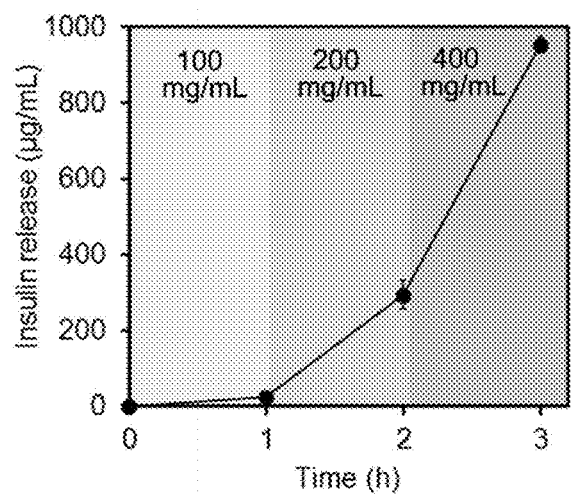

FIG. 12 shows a self-regulated insulin release profile as a function of glucose concentration.

Figure 13:
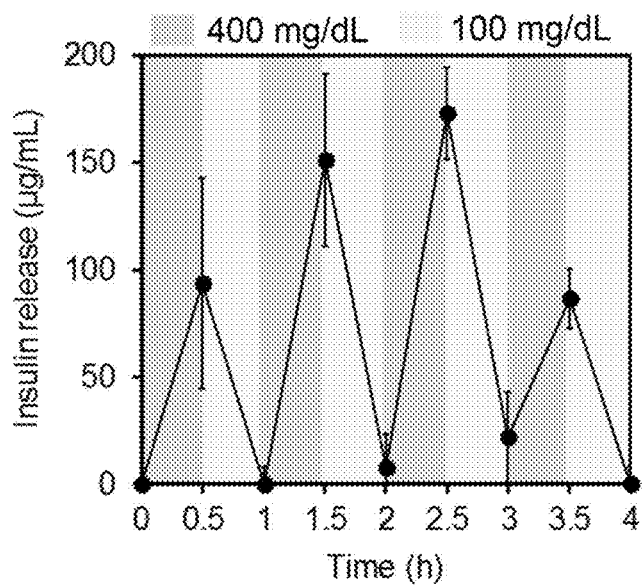

FIG. 13 shows a pulsatile insulin release profile as a function of glucose concentrations over time.

Figure 14:
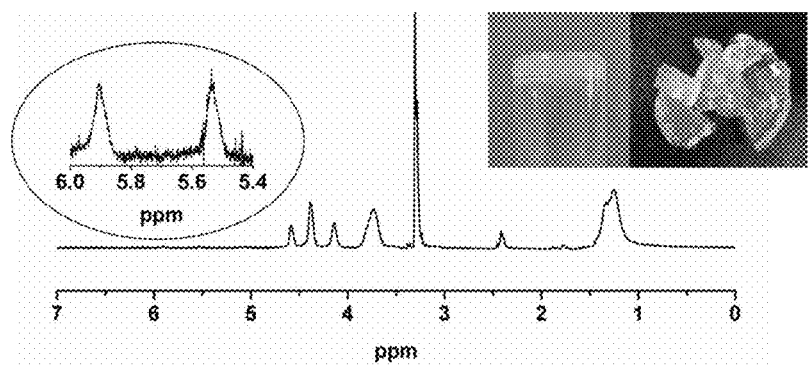

FIG. 14 shows an 1H-NMR of PVA methacrylate and its gel in aqueous solution.

Figure 15:
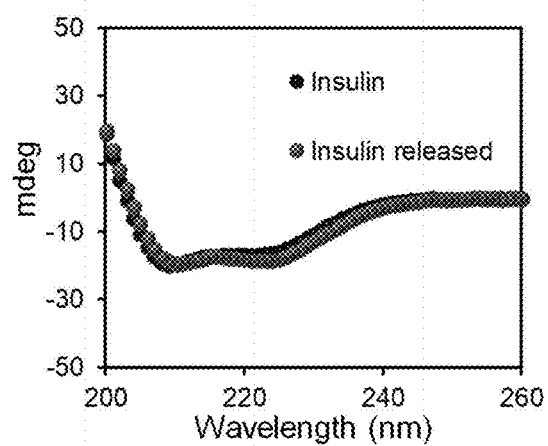

FIG. 15 shows CD spectra of native insulin solution and insulin released from the gels incubated with 400 mg/dL glucose.

Figure 16:
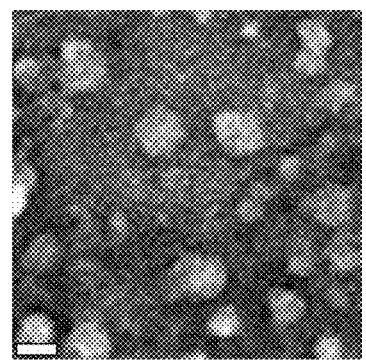

FIG. 16 shows a representative TEM image of CAT-NG. Scale bar, 20 nm.

Figure 17:
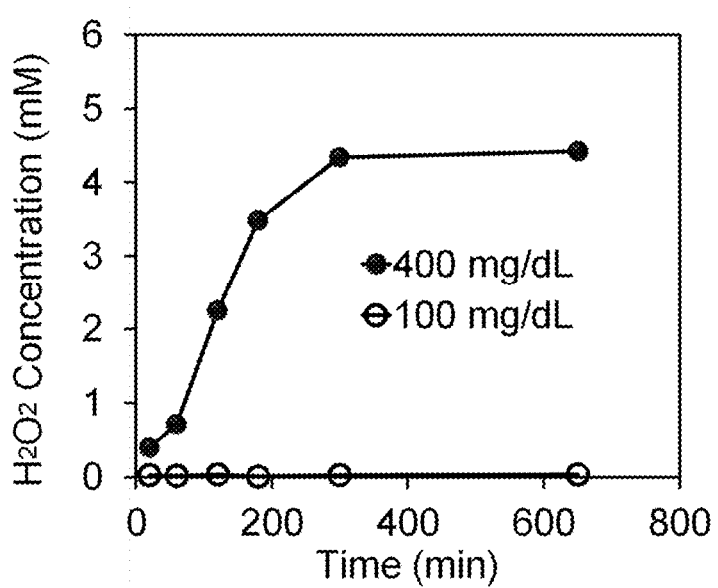

FIG. 17 shows the $H_2O_2$ generation rate through oxidation of glucose by GOx-NG in the presence of CAT-NG in glucose solution (100 or 400 mg/dL) in PBS with an initial pH at 7.4. The concentration of GOx and CAT was set to 0.2 mg/mL GOx-eq. concentration and 0.08 mg/mL CAT-eq. concentration, respectively.

Figure 18:
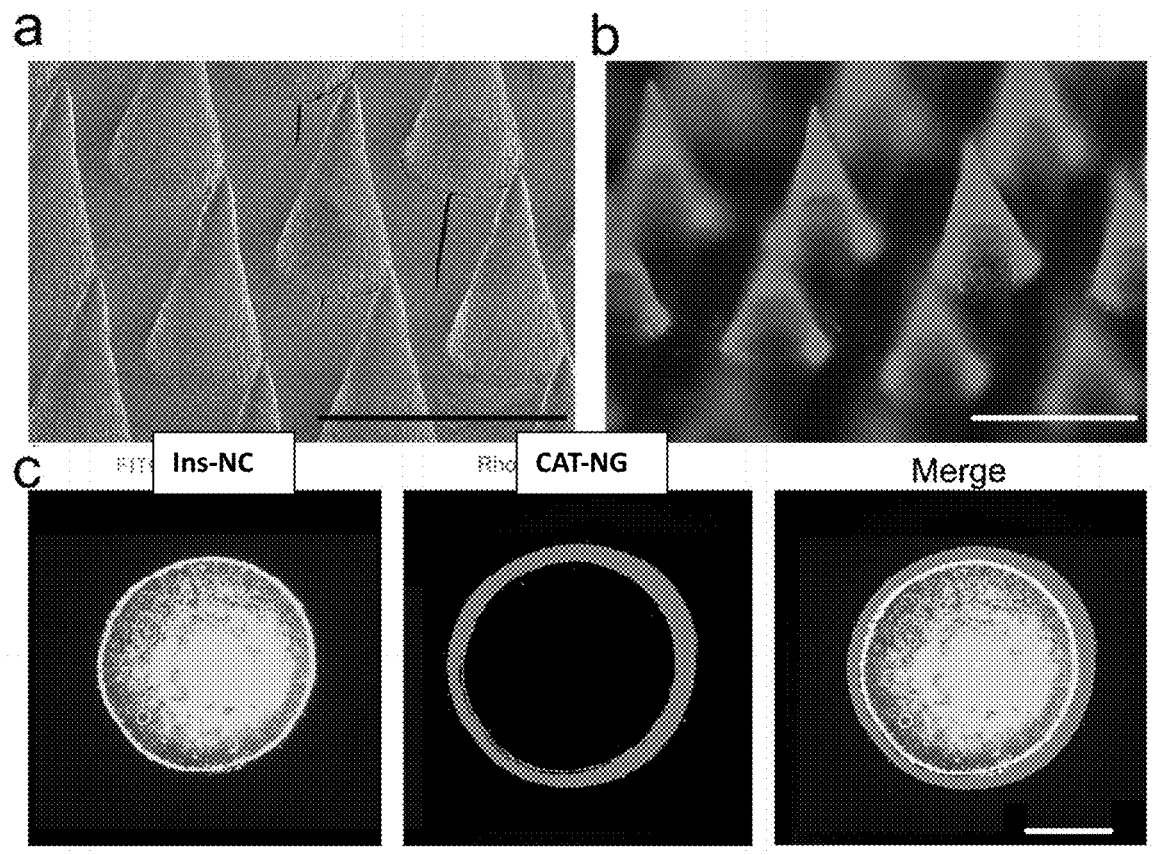

FIG. 18 shows the characterization of core-shell MN array patch. (a) Representative scanning electron microscopy image of microneedle patch. Scale bar, 600 (b) Representative fluorescence microscopy image of MN arrays loaded with rhodamine B labeled insulin. Scale bar, 600 μm. (c) Representative images of a cross-section of core-shell MN: FITC labeled CAT shell (green), rhodamine B labeled insulin (red), and merging of both images. The shell was 25±6 μm thick as analyzed using software ImageJ. Scale bar, 100 μm.

Figure 19:
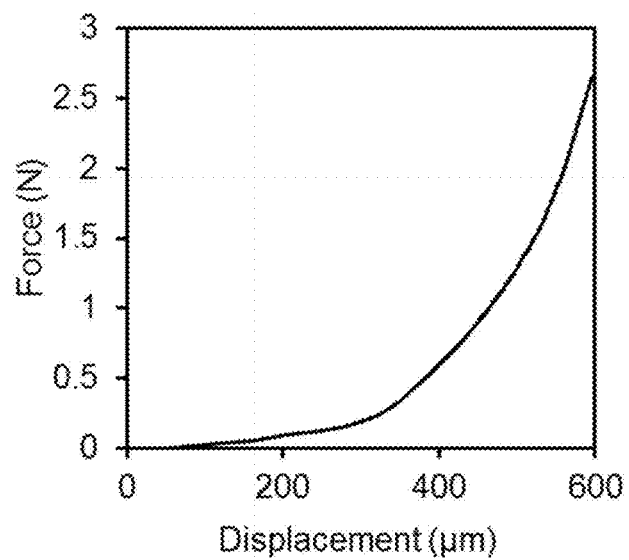

FIG. 19 shows the mechanical strength of microneedle.

Figure 20:
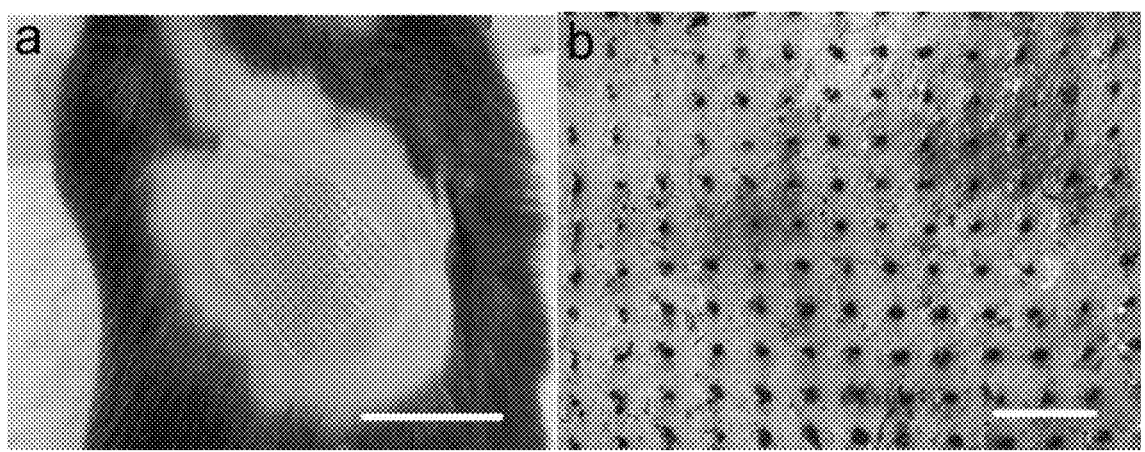

FIG. 20 shows images of a mouse treated by MN (a) and the trypan blue staining (b). Scale bars, 1 cm for (a) and 600 μm for (b).

Figure 21:

FIG. 21 shows skin puncture marks at 0, 5 and 120 min post-treatment of MNs. Scale bar, 0.5 cm.

Figure 22:
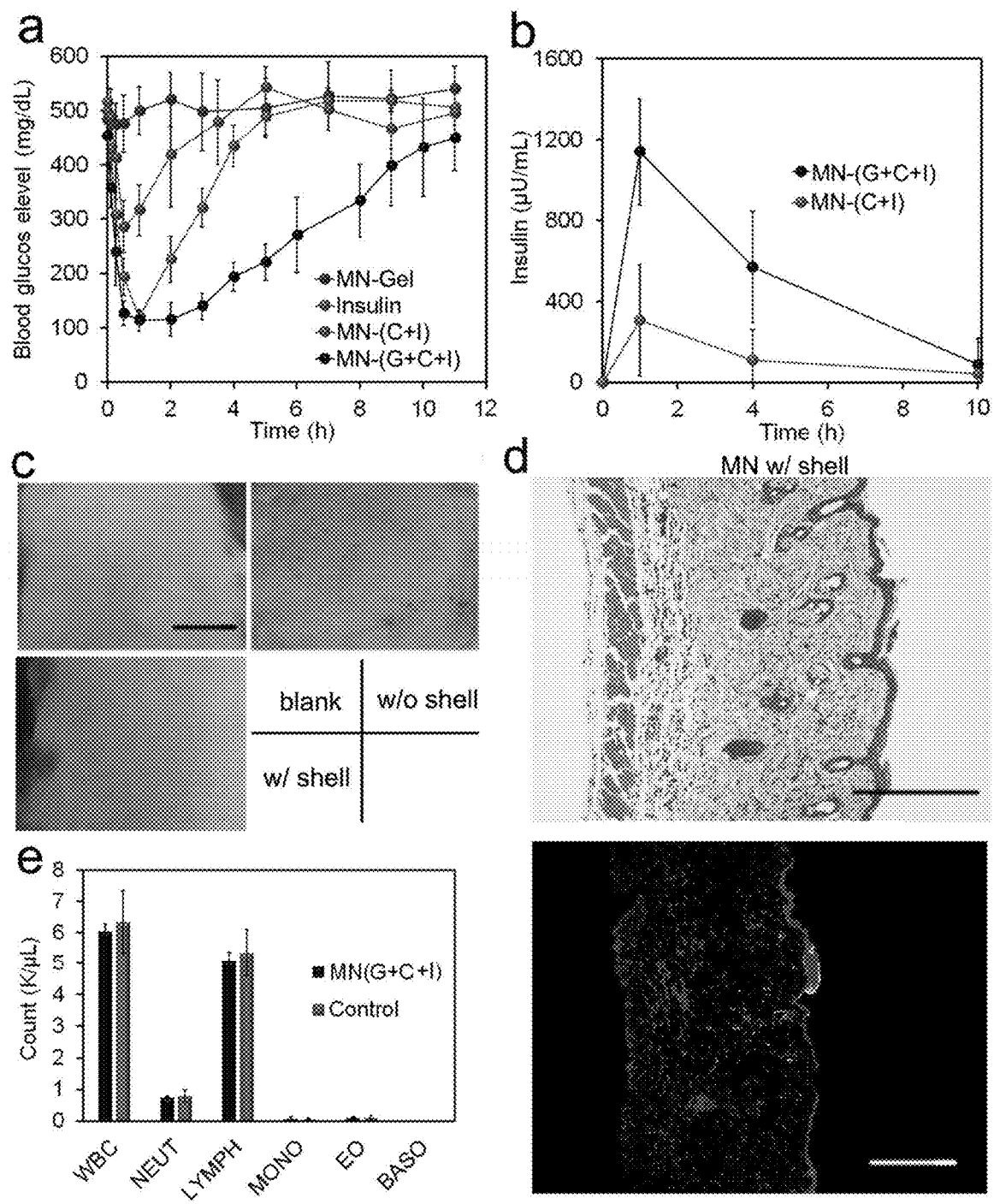

FIG. 22 shows the in vivo evaluation of MN array patches for type 1 diabetes treatment. (a) Blood glucose levels of type 1 diabetic mice treated with different kinds of microneedle array patches. (b) Blood insulin level of mice treated by MN (c) Representative images of skins at the treated site of mice. Mice were treated with MN-Gel, MN-(G+I) and MN-(G+C+I). Scale bars, 1 cm. (d) H&E staining and Immunohistologic staining with TUNEL assay (green) and Hoechst (blue) of skins treated with MN-(G+C+I). Scale bars, 300 μm. (e) Analysis of blood white cells of mice treated by MN-(G+C+I). Blood samples were obtained two days post-treatment.

Figure 23:
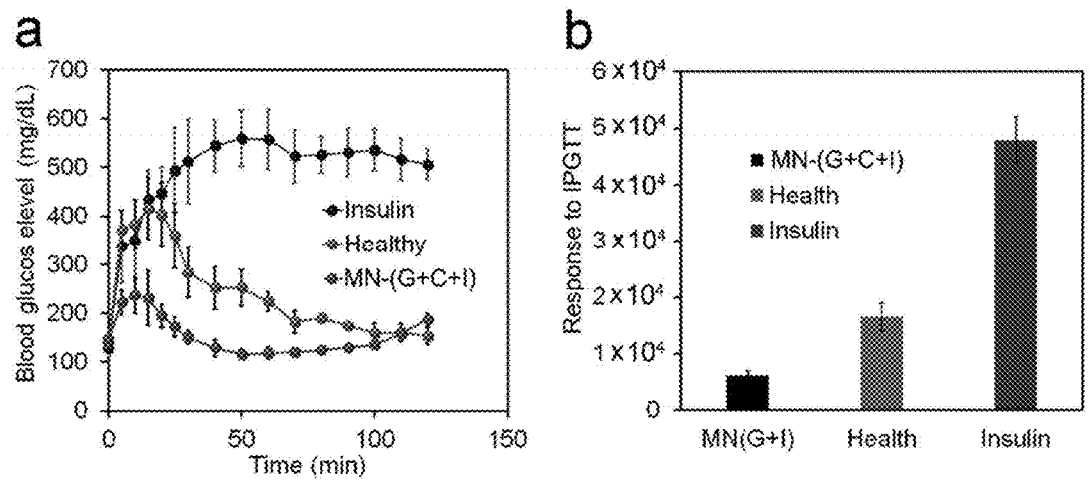

FIG. 23 shows IPGTT and responsiveness. (a) In vivo glucose tolerance test toward diabetic mice at one-hour post-treatment of MN-(G+C+I) or subcutaneously injected with insulin. Healthy mice were used as the control. (b) Responsiveness was calculated based on the area under the curve (AUC) in 120 min, with the baseline set at the 0-min blood glucose reading.

Figure 24:
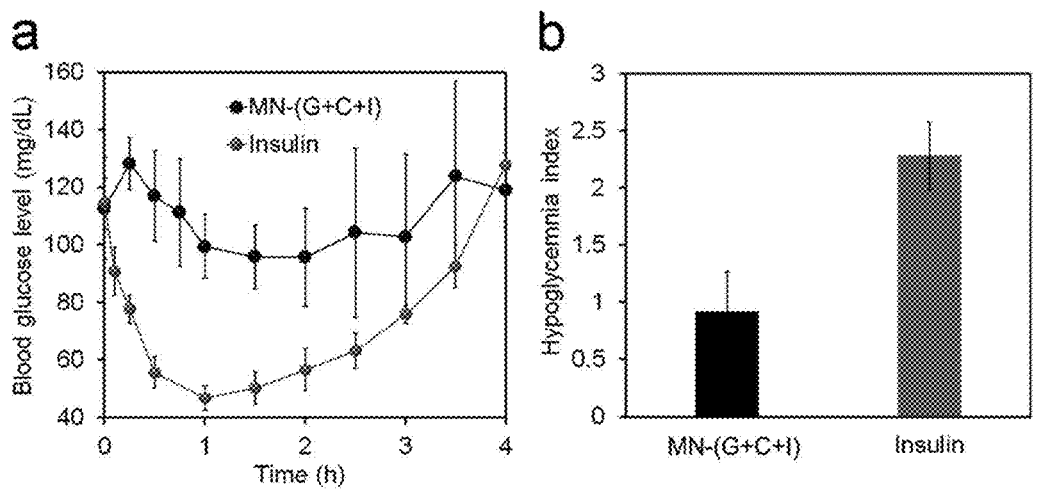

FIG. 24 shows a hypoglycemic test of MN on healthy mice. (a) Blood glucose levels change of healthy mice treated with MN array patch or subcutaneously injected insulin. The treatment was given at 0 min. (b) Quantification of the hypoglycemia index, identified as the difference between the initial and nadir blood glucose readings divided by the time at which nadir was reached.

Figure 25:
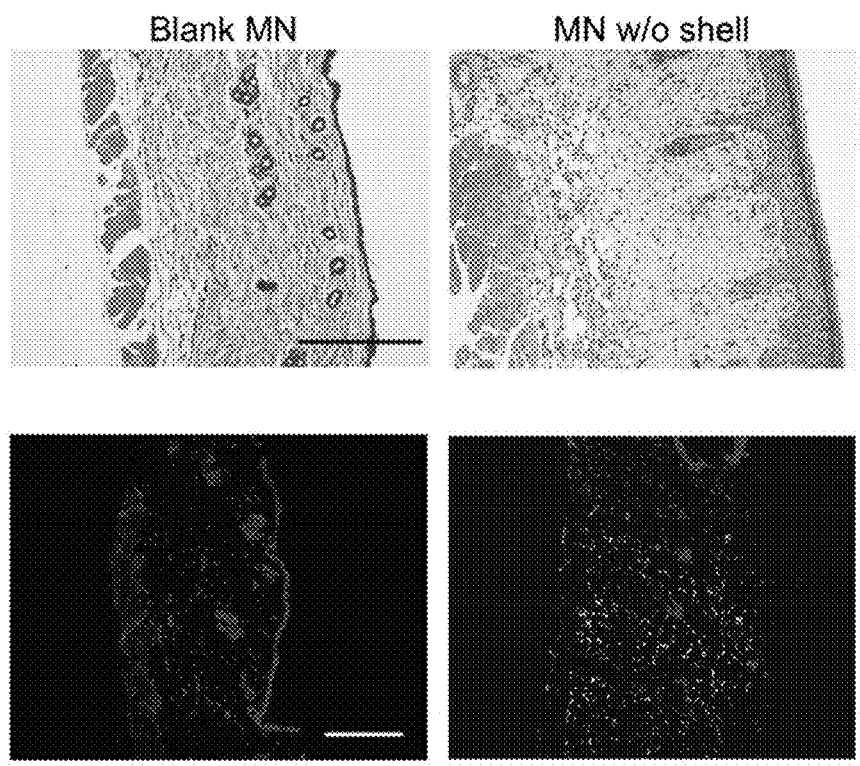

FIG. 25 shows H&E staining and Immunohistologic staining results of skins treated by blank MN and MN-(G+I). Scale bars, 300 μm.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Terminology

Unless defined otherwise, all technical and scientific terms used herein have the same meaning as commonly understood to one of ordinary skill in the art to which this invention belongs. The following definitions are provided for the full understanding of terms used in this specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In one non-limiting embodiment, the terms are defined to be within 10% of the associated value provided. In another non-limiting embodiment, the terms are defined to be within 5%. In still another non-limiting embodiment, the terms are defined to be within 1%.

"Administration" to a subject includes any route of introducing or delivering to a subject an agent. Administration can be carried out by any suitable route, including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "control" is an alternative subject or sample used in an experiment for comparison purposes. A control can be "positive" or "negative."

"Controlled release" or "sustained release" refers to release of an agent from a given dosage form in a controlled fashion in order to achieve the desired pharmacokinetic profile in vivo. An aspect of "controlled release" agent delivery is the ability to manipulate the formulation and/or dosage form in order to establish the desired kinetics of agent release.

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount"

of an agent necessary to achieve a therapeutic effect may vary according to factors such as the age, sex, and weight of the subject. Dosage regimens can be adjusted to provide the optimum therapeutic response.

For example, several divided doses may be administered daily or the dose may be proportionally reduced as indicated by the exigencies of the therapeutic situation.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., Type 1 diabetes). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

Publications cited herein are hereby specifically incorporated by reference in their entireties and at least for the material for which they are cited.

C. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular microneedle patch is disclosed and discussed and a number of modifications that can be made to a number of micelles including polymer composition of the micelles shell and any insulin, glucose responsive enzyme, or $H_2O_2$ scavenger are discussed, specifically contemplated is each and every combination and permutation of the microneedle patch and the modifications that are possible unless specifically indicated to the contrary.

Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Figure 1:
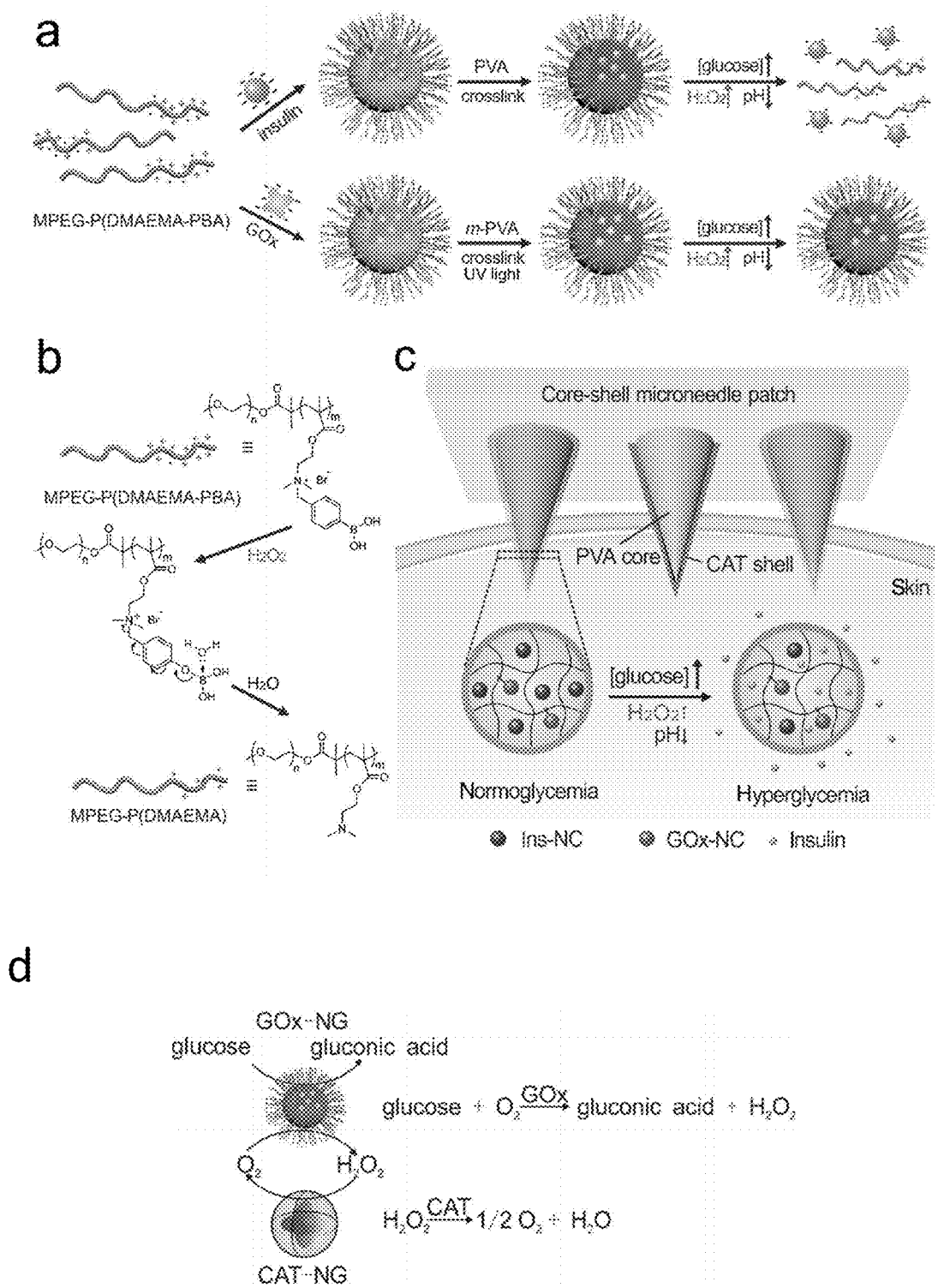

Here, a new glucose-responsive microneedle (MN) array patch for self-regulated insulin delivery is described, utilizing $H_2O_2$ and pH cascade-responsive nano-sized complex micelles (NCs) are disclosed. Briefly, insulin is first entrapped into degradable complex micelles (designated Ins-NC); while a glucose responsive enzyme (such as, for example, GOx) is encapsulated into nondegradable complex micelles (designated GOx-NC)(see, FIG. 1).

In one aspect, the nano-sized complex micelles in the microneedle patches can comprise diblock copolymer micelles such as, for example, mPEG$_n$-poly(2-(dimethylamino)ethyl methacrylate-4-(bromomethyl)phenylboronic acid)$_m$ as shown in Formula 1

Formula I

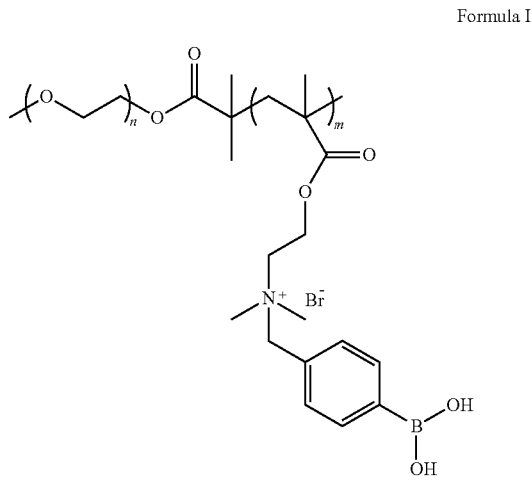

and abbreviated herein as (MPEG$_n$-P(DMAEMA-PBA)$_m$); wherein n, represents the number of MPEG repeats and can any number of repeats be between about 1 and about 8,000 repeats, preferably, between about 2K and about 6K repeats, most preferably, between about 4.5K and about 5.5K repeats (for example 1, 2, 3, 4, 5, 6, 7, 8, 9, 10, 10, 30, 40, 50, 60, 70, 80, 90, 100, 200, 300, 400, 500, 600, 700, 800, 900, 1K, 1.1K, 1.2K, 1.3K, 1.4K, 1.5K, 2K, 2.5K, 3K, 3.5K, 4K, 4.5K, 4.6K, 4.7K, 4.8K, 4.9K, 5K, 5.1K, 5.2K, 5.3K, 5.4K, 5.5K, 6K, 6.5K, 7K, 7.5K, or 8K; and wherein m represents the number of P(DMAEMA-PBA) repeats can any number of repeats be between about 1 and about 18,000 preferably, between about 4K and about 16K repeats, most preferably between about 6K and about 14K repeats (for example 1, 2, 3, 4, 5, 6, 7, 8, 9, 10, 10, 30, 40, 50, 60, 70, 80, 90, 100, 200, 300, 400, 500, 600, 700, 800, 900, 1K, 1.1K, 1.2K, 1.3K, 1.4K, 1.5K, 2K, 2.5K, 3K, 3.5K, 4K, 4.5K, 4.6K, 4.7K, 4.8K, 4.9K, 5K, 5.1K, 5.2K, 5.3K, 5.4K, 5.5K, 6K, 6.5K, 7K, 7.5K, 8K, 8.5K, 9K, 9.5K, 10K, 10.5K, 11K, 11.5K, 12K, 12.5K, 13K, 13.5K, 14K, 14.5K, 15K, 15.5K, 16K, 16.5K, 17K, 17.5K, or 18K. For example, disclosed herein are microneedle patches comprising micelles comprising insulin and/or a glucose responsive enzyme, wherein the micelle comprises MPEG$_{5K}$-P(DMAEMA-PBA)$_{14K}$ or MPEG$_{5K}$-P(DMAEMA-PBA)$_{6K}$.

It is understood and herein contemplated that there are numerous diblock copolymers that can be utilized to form the micelles of the present disclosure beyond the MPEG$_n$-P(DMAEMA-PBA)$_m$ exemplified herein, including but not limited to primary, secondary, and tertiary amines.

The diblock copolymer micelles that are incorporated in the disclosed microneedle patches can comprise insulin and the glucose responsive enzyme (such as, for example, glucose oxidase (GOx)) separately or in the same micelle. As the glucose levels rise in the tissue surrounding the microneedle patch, glucose diffuses across the micelle and is oxidized (as shown in FIG. 1D) into gluconic acid and $H_2O_2$. The decreased pH from the formation of gluconic acid and the increase in $H_2O_2$ degrade the micelle core surrounding the insulin resulting in insulin release and also results in the dissociation of the micelle form the microneedle due to the acidic and oxidative conditions. Thus, upon painless transcutaneous administration, only Ins-NC can be decomposed when MN is exposed to interstitial fluid in the capillary networks under a hyperglycemic state, thereby releasing insulin for quick uptake through the regional capillary vessels and lymph networks to subsequently regulate BGLs.

It is understood and herein contemplated that the production of $H_2O_2$ can result in long-term incompatibility of the microneedle patch. Inspired by the protection function against oxidation in the peroxisome, catalase nanogel (CAT-NG) is embedded into the crosslinked-PVA shell, covering the surface of the microneedle core (FIG. 1c), to mitigate the injury of $H_2O_2$ generated in the core part toward normal tissues (FIG. 1d). Stated more simply, to prevent long-term incompatibility of $H_2O_2$, the disclosed microneedles can be coated with $H_2O_2$ scavenging enzyme. Examples of $H_2O_2$ scavenging enzymes include, but are not limited to catalase, phenolic acid, 3,4,5-trihydroxybenzoic (gallic) acid and 1,2,3-trihydroxybenzene (pyrogallol). The $H_2O_2$ scavenging enzymes can be incorporated into the microneedle by any means known in the art, including incorporation of the $H_2O_2$ scavenging enzyme in a nanogel (for example a peroxisome catalase nanogel).

To stabilize the micelles, the core of the micelle can comprise a poly(vinyl alcohol) (PVA) or methacrylate PVA (m-PVA). Other examples of diblock copolymers that can be used in the micelles disclosed herein comprise a polymer such as, example, polyethylene glycol (PEG), polyvinyl acetate, polyvinyl alcohol (PVA), polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic) acid, poly(lactic co-glycolic) acid (PLGA), cellulose derivatives, such as hydroxymethylcellulose, hydroxypropylcellulose and the like. The stabilization occurs via cross-linking via acid-inert ester bonds between the phenylboronic acids of P(DMAEMA-PBA) and cis-1, 3-diols on PVA. In one aspect, the crosslinking of the micelles incapsulating insulin can be degradable. The crosslinking of m-PVA in the micelles incapsulating the glucose responsize enzyme can form non-cleavable covalent bonds (FIG. 1a). Both Ins-NC and GOx-NC can be loaded into the crosslinked gel core of microneedle. This loading can occur, in one aspect, by crosslinking the micelle to the microneedle core. Thus, in one aspect, disclosed herein are microneedles comprising a core, wherein the glucose responsive enzyme comprising micelles can be crosslinked to the microneedle core via uncleavable covalent bonds (for example, between the microneedle core and m-PVA).

It is understood and herein contemplated that under a hyperglycemic condition, the Ins-NC can respond to $H_2O_2$ and gluconic acid generated by the GOx-catalyzed oxidation of glucose and be dissociated to promote insulin release because of the disruption of micelle structure as well as charge reductions of polymer (positive charge) and insulin (negative charge) (FIG. 1a-b). Accordingly, in one aspect, disclosed herein are particles of any preceding aspect, wherein the micelle is degradable in a relatively acidic pH compared to physiological pH (approximately between 7.35-7.45). For example, the pH can be reduced to a pH of 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, or 4.0.

In one aspect, the disclosed microneedle patches can comprise a plurality of microneedles, wherein the plurality of microneedles have a center-to-center interval of about 200 μm to about 800 μm, for example a center to center interval of about 200, 225, 250, 275, 300, 325, 350, 375, 400, 425, 450, 475, 500, 525, 550, 575, 600, 625, 650, 675, 700, 725, 750, 775, or 800 μm.

It is also understood and herein contemplated that the disclosed plurality of microneedles in the microneedle patches is effective when the length of the needle is sufficiently long to reach desired tissues below the dermal layer. Thus, in one aspect, disclosed herein are devices wherein the plurality of microneedles have a height of about 600 nm to 1.8 μm. For example, the plurality of microneedles can have a height of about 600, 650, 700, 750, 800, 850, 900, 950 nm, 1.0, 1.1, 1.2, 1.3, 1.4, 1.5, 1.6, 1.7, or 1.8 μm.

In one aspect, the disclosed microneedle patches can be a component of a self-regulating insulin delivery system.

The disclosed microneedle patches can provide self-regulating administration of insulin to a subject in need thereof. Thus, in one aspect, disclosed herein are methods of treating hyperglycemia (such as, for example, hyperglycemia in a diabetic subject) in a subject comprising administering to the subject the microneedle patch of any preceding aspect. Thus, for example, disclosed herein are methods of treating diabetes (such as Type I or Type II diabetes) in a subject comprising administering to the subject a microneedle patch comprising diblock copolymer micelles; wherein the diblock copolymer micelles comprise separately insulin and glucose oxidase; wherein the microneedles are coated with $H_2O_2$ scavenging enzyme; and wherein the insulin dissociates from the micelle in an acidic and oxidative environment.

As used herein, "Type I diabetes" refers to the form of diabetes mellitus resulting from the autoimmune destruction of insulin-producing cells and reduction of the body's ability to produce insulin. The loss of insulin results in increased blood sugar.

"Treat," "treating," "treatment," and grammatical variations thereof as used herein, include the administration of a composition with the intent or purpose of partially or completely preventing, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

D. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Figure 2:
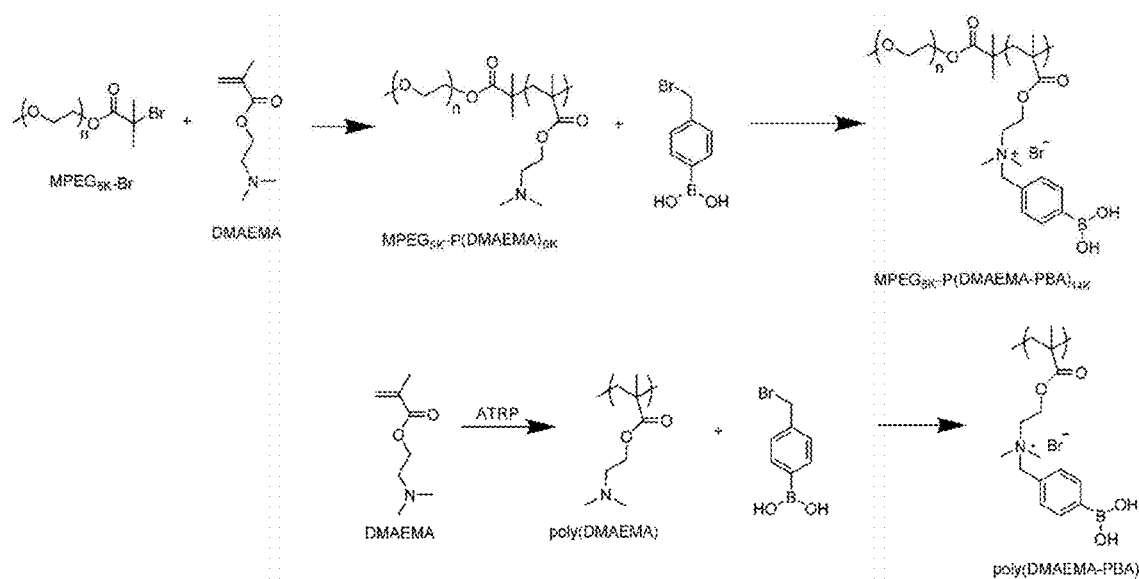
FIG. 2 shows synthetic routes of polymers.
Figure 3:
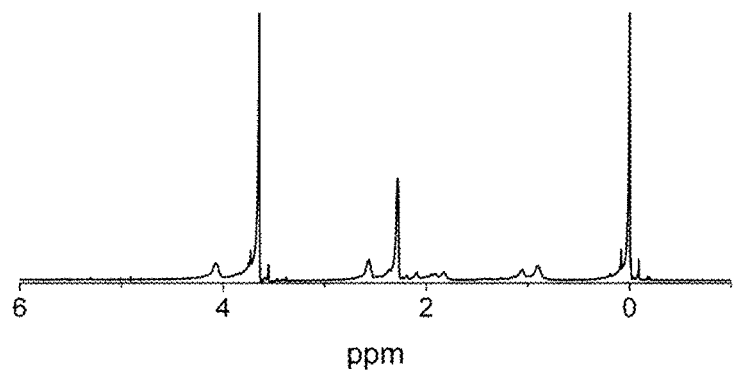
FIG. 3 shows 1H-NMR spectrum of $MPEG_{5K}$-P(DMAEMA)$_{6K}$.
Figure 4:
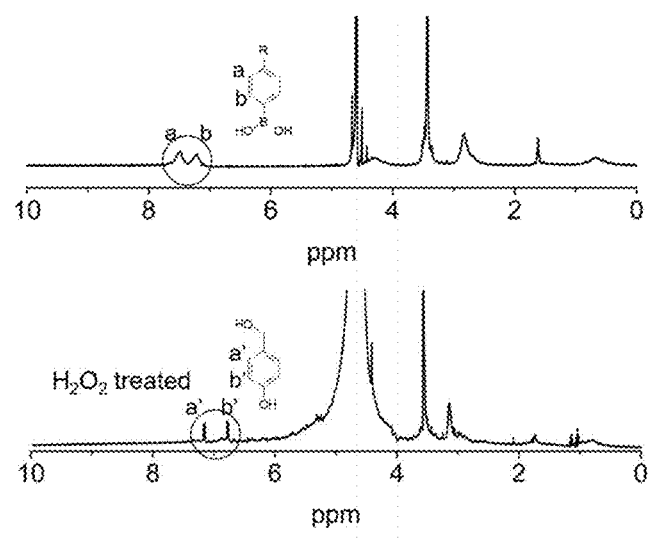
FIG. 4 shows 1H-NMR spectra of $MPEG_{5K}$-P(DMAEMA-PBA)$_{14K}$ before and after $H_2O_2$ (80 mM) treatment.
Figure 5:
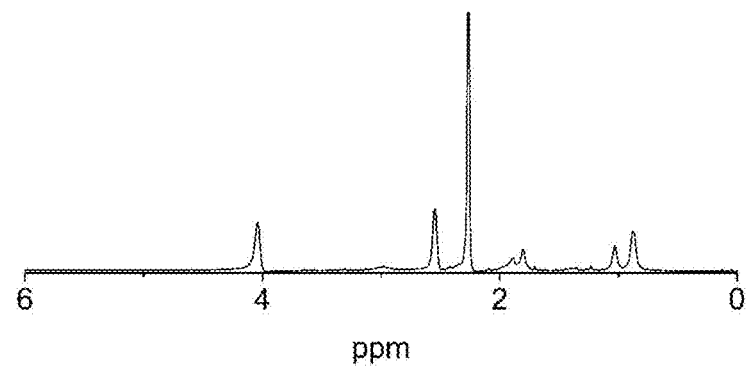
FIG. 5 shows an 1H-NMR spectrum of poly(DMAEMA) synthesized by ATRP initiated by ethyl α-bromoisobutyrate.
Figure 6:
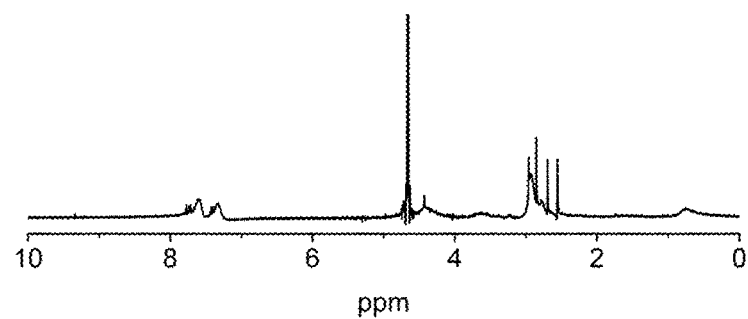
FIG. 6 shows 1H-NMR spectrum of poly(DMAEMA-PBA).

Through the atom transfer radical polymerization (ATRP) initiated by MPEG$_{5K}$-Br, 2-(dimethylamino)ethyl methacrylate (DMAEMA) was polymerized to obtain MPEG5K-P(DMAEMA)$_{6K}$ (FIGS. 2 and 3), which was subsequently modified with 4-(bromomethyl)phenylboronic acid to obtain the positively charged MPEG$_{5K}$-P(DMAEMA-PBA)$_{14K}$ (FIG. 4). In the presence of $H_2O_2$, phenylboronic acid on MPEG$_{5K}$-P(DMAEMA-PBA)$_{14K}$ was oxidized and hydrolyzed, generating MPEG$_{5K}$-P(DMAEMA)$_{6K}$ with reduced positive charge (FIG. 1b), as demonstrated by 1H-NMR (FIG. 4). Also, poly(DMAEMA) and poly(DMAEMA-PBA) were synthesized via ATRP initiated by ethyl α-bromoisobutyrate and subsequent quaternarization by 4-(bromomethyl)phenylboronic acid, respectively (FIGS. 5 and 6). Given its isoelectric point of ~5.3 insulin is negatively charged at pH 7.4 and capable of complexing with positively charged MPEG$_{5K}$-P(DMAEMA-PBA)$_{14K}$ to form Ins-NC with a PEG corona and a complex core To further stabilize the micelle structure, poly(vinyl alcohol) (PVA) was incorporated via forming acid-inert ester bonds between the phenylboronic acids on poly(DMAEMA-PBA) and cis-1, 3-diols on PVA Therefore, Ins-NCs with a loading capacity of 50 wt %, an average hydrodynamic size around 60 nm, and ζ-potential of 4.4±0.5 mV were achieved, as determined by dynamic light scattering (DLS) (FIG. 7a) and transmission electronic microscopy (TEM) (FIG. 7b). When Ins-NC was degraded, the solution gradually became transparent after incubation with glucose (400 mg/dL) in the presence of GOx (FIG. 8). Meanwhile, GOx was also integrated into nano-complex micelles (GOx-NC) with an average hydrodynamic size around 50 nm and -potential of 2.1±0.4 mV. In addition, GOx-NC formed an undegradable network with MPEG$_{5K}$-P(DMAEMA-PBA)$_{14K}$ and crosslinked by PVA methacrylate (m-PVA) (FIG. 9) upon exposure to UV light (365 nm, 6×10 s). GOx-NC had a GOx loading capacity of 33 wt %, and showed similar activity to native GOx regarding catalyzing the oxidation of glucose to produce $H_2O_2$ and gluconic acid (FIG. 7c-d). Next, the insulin release rate was evaluated in the presence of GOx in phosphate buffered saline (PBS) at pH 7.4 with three different glucose concentrations, including a typical hyperglycemic level (400 mg/dL), a normoglycemic level (100 mg/dL), and a control level (0 mg/dL). The insulin release rate was remarkably promoted under a hyperglycemic state compared to those of other two groups (FIG. 10a).

Furthermore, the mechanism of glucose-triggered insulin release was investigated. Prior to PVA crosslinking, instant insulin release was triggered in both 100 or 400 mg/dL glucose solution (FIG. 11). However, the addition of PVA stabilized the micelles and significantly reduced insulin release in 100 mg/dL glucose solution (FIG. 10a). Further studies indicated that neither $H_2O_2$ or slightly acidic environment could individually achieve insulin release (FIG. 10b). Moreover, insulin was found to be instantly released in slightly acidic pH from the complex that was treated beforehand by $H_2O_2$, indicating that the insulin was released in a cascade: 1) poly(DMAEMA-PBA) was oxidized and hydrolyzed to poly(DMAEMA), leading to reduced positive charge of polymer and crosslinking density of Ins-NC; 2) the gradually reduced pH led to reduced negative charge or even charge reversal of insulin (from negative to positive charge), thereby resulting in the dissociation of complex and subsequent release of insulin. This two-step pattern of insulin release endows the insulin delivery system enhanced safety for in vivo application to avoid the unwanted insulin release solely triggered by either $H_2O_2$ or acid, for example, generated in a non-relevant condition of inflammation. Moreover, the release rate of insulin from complex was steadily enhanced when gradually increasing the glucose concentrations of the tested solutions from normoglycemic to hyperglycemic conditions, where a 50-fold difference in insulin release rate was achieved in one hour when the glucose concentration was increased from 100 to 400 mg/dL (FIG. 12). Additionally, the pulsatile release profile of insulin was achieved when the complex was alternatively exposed to the normal and hyperglycemic levels (FIG. 13).

The insulin and GOx release profiles from nano-complex micelles encapsulated in m-PVA gel were critical for their in vivo application. The m-PVA gel was prepared from m-PVA aqueous solution via exposure to UV light in the presence of a radical initiator (FIG. 14). The release rate of insulin from Ins-NC entrapped in the gel was three-fold faster at a glucose concentration of 400 mg/dL than that of 100 mg/dL (FIG. 10c). Meanwhile, the release rate of GOx was independent on glucose level and occurred in negligible amounts due to the crosslinking of GOx-NC by m-PVA. Additionally, the far-UV circular dichroism (CD) spectra of the native and released insulin from gels were nearly identical, indicating that the released insulin retained a-helical secondary structure associated with bioactivity (Supplementary FIG. 15).

To facilitate the administration, Ins-NC and GOx-NC were integrated into a painless transdermal MN array patch. The core-shell MN array patch was prepared using a micromolding approach. First, the CAT was encapsulated into a CAT-NG to inhibit passive release of CAT (FIG. 16). CAT-NG retained activity of catalyzing $H_2O_2$ to $H_2O$ (FIG. 17), and was then dissolved in an aqueous solution containing m-PVA, loaded into a silicone micromold and kept under reduced pressure for 30 min. After centrifugation, it was exposed to UV light for a brief time to crosslink the matrix to form a MN "shell". Ins-NC, GOx-NC and radical initiator dissolved in an aqueous solution containing PVA/m-PVA and polyvinylpyrrolidone (PVP) were then deposited in silicone molds to form a MN "core". The addition of a proper ratio of PVP has been shown to enhance the strength of microneedle for better skin penetration. The resulting device was arranged in a 20×20 MN array on a patch. The needle had a conical shape (FIG. 18a-b) and enough strength (FIG. 19). In addition, FITC-labeled CAT-NG formed a shell covering on the PVA/m-PVA/PVP core loaded with the rhodamine B-labeled insulin as validated using fluorescence microscope (FIG. 18c).

The in vivo performance of the core-shell MN array patches was evaluated utilizing a mouse model of type 1 diabetes induced by streptozotocin (STZ). The mice were divided into four groups treated with 1) CAT-NG shelled MN array patch loaded with GOx-NC and Ins-NC (MN-(G+C+I)); 2) subcutaneous injection of human recombinant insulin; 3) microneedle array patch loaded with blank PVA/m-PVA and PVP (MN-Gel); 4) CAT-NG shelled MN array patch of Ins-NC (MN-(C+I)). The staining by trypan blue indicated successful penetration of MNs into the excised skin (FIG. 20). Besides, the temporal microchannels on the skin caused by MNs could quickly recover within two hours post-treatment (FIG. 21).

BGLs of the mice were monitored over time following treatment with MN patches. It was observed that the BGLs of mice treated by MN-(G+C+I) were quickly decreased to around 100 mg/dL in 30 min post-administration and maintained below 200 mg/dL for almost 4 hours, considerably longer than those of the mice subcutaneously injected with insulin (FIG. 22a). This fast dynamic in BGL change was attributed to the rapid establishment of local oxidative and the acidic environment through oxidation of glucose in the presence of GOx-NC, as well as the high sensitivity of Ins-NC to these stimuli. In contrast, the negligible BGLs reduction was observed in the mice treated with MN-(C+I) and MN-Gel. Additionally, the plasma human insulin levels in mice treated with MN-(G+C+I) was significantly higher than those treated with MN-(C+I) (FIG. 22b).

Moreover, the intraperitoneal glucose tolerance test (IP-GTTs) was further carried out one-hour post-administration of MNs or insulin. A spike in BGLs was observed for all groups after the Intraperitoneal injection of glucose. However, only healthy mice and MN-(G+C+I) were able to restore blood glucose levels to a normoglycemic level within a short period, and the mice treated with MN-NC(G+C+I) showed significantly enhanced glucose tolerance to the glucose challenge (FIG. 23). To assess the risk of hypoglycemia associated with treatment by MN-NC(G+C+I), the BGLs of healthy mice treated with different MN array patches were observed. The BGLs of mice treated with insulin showed a remarkable decrease, while the BGLs of mice treated with MN-(G+C+I) showed only a slight decrease, consistent with the slow release of insulin from gels under a normoglycemic state (FIG. 24a). Additionally, the MN-(G+C+I) treated group showed significantly lower hypoglycemia index than insulin (FIG. 24b).

Importantly, compared to the skin tissues treated by MN-Gel (FIG. 22c), a clear damage of skin tissue was observed for MN-(G+I). In sharp contrast, only negligible inflammation was observed on the skin of mice treated with MN-(G+C+I) due to the presence of a CAT-embedded shell (FIG. 22c). These findings were further validated by hematoxylin and eosin (H&E) staining results. Compared with the skin treated with MN-Gel (FIG. 25), the skin samples treated with MN-(G+I) (FIG. 25) were significantly thicker and showed obvious neutrophil infiltration, indicating a pathophysiological response and tissue damage induced by $H_2O_2$. However, reduced neutrophil infiltration was observed in skin samples from mice treated with MN-(G+C+I) (FIG. 22d). Additionally, the skin tissue stained with the in situ TUNEL assay clearly demonstrated the cell apoptosis in the skin sample treated with MN-(G+I) compared to that associated with the control group (FIG. 22d). Accordingly, the counts of white blood cells from mice treated by MN-(G+C+I) were similar to that of the normal mice (FIG. 22e).

In summary, a novel core-shell MN-array patch loaded with dual sequential stimuli-responsive nano-complex micelles has been developed for self-regulated insulin delivery. It was demonstrated that this patch could rapidly and safely release insulin triggered by locally generated $H_2O_2$ and an acidic microenvironment under a hyperglycemic condition. In vivo experiments indicated that the MN-(G+C+I) was effective in regulating BGLs under a normoglycemic state while reducing the risk of hypoglycemia. Importantly, utilization of CAT coating significantly mitigated the skin inflammation caused by the production of $H_2O_2$. This design offers a broad platform for transdermal drug delivery in a physiological signal-controlled manner with enhanced biocompatibility.

a) Materials and Methods (1) Materials.

4-(Bromomethyl) phenylboronic acid was purchased from Boron Molecular. All other chemical reagents were purchased from Sigma-Aldrich. Insulin was purchased from Gibco. $MPEG_{5K}$-Br was synthesized as reported.[1]

(2) Synthesis (a) Synthesis of $MPEG_{5K}$-P(DMAEMA)$_{6K}$.

$MPEG_{5K}$-Br (0.2 g, 0.04 mmol), CuBr (5.7 mg, 0.04 mmol) and 1, 4-bipyridine (12.5 mg. 0.08 mmol) were added to a round bottom flask and protected with $N_2$ atmosphere. To this mixture, THF (2 mL) and DMAEMA (0.2 g, 1.3 mmol) were added sequentially and mixed gently. After three freeze-thaw cycles, the flask was sealed with $N_2$, immersed into oil bath and stirred overnight at 60° C. The resultant solution was poured into ethyl acetate (100 mL) and washed with $NaHCO_3$ (0.1 N, 3×50 mL) and dried over anhydrous $NaSO_4$. After filtration and removing solvent, slightly yellow viscous solid was obtained (0.2 g, yield 50%). 1H-NMR (300 MHz, $CDCl_3$) was shown in FIG. 3.

(b) Synthesis of $MPEG_{5K}$-P(DMAEMA-PBA)$_{6K}$.

$MPEG_{5K}$-P(DMAEMA)$_{6K}$ (0.11 g, 0.01 mmol) and 4-(bromomethyl)phenylboronic acid (0.5 g, 2.3 mmol) were dissolved in DMF separately and mixed. The mixture was stirred at 60° C. overnight and dialysis against $H_2O$ (3×2 L). After filtration and lyophilization, white product was obtained (0.15 g, yield 75%). 1H-NMR (300 MHz, $D_2O$) was shown in FIG. 4.

(c) Synthesis of Poly(DMAEMA).

DMAEMA (0.2 g, 1.3 mmol), CuBr (5.7 mg, 0.04 mmol), Ethyl a-bromoisobutyrate (8 mg, 004 mmol), and 1, 4-bipyridine (12.5 mg. 0.08 mmol) were added to a round bottom flask and protected with $N_2$ atmosphere. To this mixture, THF (2 mL) and DMAEMA (0.2 g, 1.3 mmol) were added sequentially and mixed gently. After three freeze-thaw cycles, the flask was sealed with $N_2$, immersed into an oil bath and stirred overnight at 60° C. The resulted solution was poured into ethyl acetate (100 mL) and washed with $NaHCO_3$ (0.1 N, 3×50 mL) and dried over anhydrous $NaSO_4$. After filtration and removing the solvent, slightly yellow viscous solid was obtained and was used directly (0.15 g, yield 75%). 1H-NMR (300 MHz, $D_2O$) was shown in FIG. 5.

(d) Synthesis of Poly(DMAEMA-PBA).

Poly(DMAEMA) (0.1 g) and 4-(bromomethyl) phenylboronic acid (0.5 g, 2.3 mmol) were dissolved in DMF separately and mixed. The mixture was stirred at 60° C. overnight and dialysis against $H_2O$ (3×2 L). After filtrated and lyophilized, white product was obtained. 1H-NMR (300 MHz, $D_2O$) was shown in FIG. 6.

(e) Synthesis of Poly(Vinyl Alcohol) Methacrylate.

Poly(vinyl alcohol) (1 g) and methyl anhydride (1 g) were dissolved in DMSO (20 mL), and $Et_3N$ (1 mL) was added as a catalyst. The mixture was stirred overnight at room temperature and dialysis against $H_2O$ (3×2 L) and lyophilized to obtain the product. 1H-NMR (300 MHz, $D_2O$) was shown in FIG. 14.

(f) Rhodamine B or FITC Labeled Insulin or CAT.

Rhodamine B isothiocyanate (0.5 mg) dissolved in DMSO (1 mL) was added to insulin (20 mg) dissolved in $NaHCO_3$ aqueous solution (10 mM, 1 mL). The mixture was stirred for one hour and dialysis against $H_2O$ (3×2 L). The resultant solution was lyophilized to obtain rhodamine B labeled insulin. Other fluorescence labeled proteins were obtained with the same methods. The fluorescently labeled insulin or CAT were used in the same way as the one not labeled, and the fluorescence images were taken on a fluorescence microscope (Olympus, IX71).

(3) $H_2O_2$ Generation Rate Assay in Glucose Solution in the Presence of GOx-NC or Native GOx.

The $H_2O_2$ concentration in solution was evaluated using a fluorometric hydrogen peroxide assay kit according to the manufacturer's protocol (Sigma-Aldrich). Glucose solutions (100 or 400 mg/dL) containing GOx-NC or GOx (0.2 mg/mL) were incubated at 37° C. Samples (10 μL each tube) were withdrawn and diluted at timed intervals, and the fluorescence intensity was detected.

(4) Preparation of Insulin-NC or GOx-NC.

Typically, insulin (2 mg/mL) and $MPEG_{5K}$-P(DMAEMA-PBA)$_{14K}$ (1 mg/mL) was mixed, and the pH was adjusted to 7.4. During this process, complex micelles were generated, and PVA (for insulin-NC) or PVA methacrylate (for GOx-NC) was added as a stabilizer to obtain insulin-NC or GOx-NC.

(5) In Vitro Insulin Release from Complex of Insulin and Poly(DMAEMA-PBA).

Complex was suspended in 10 mM PBS at pH 7.4 and allocated to centrifuge tubes. Various amounts of glucose (0, 100 or 400 mg/dL final concentration) and GOx (0.2 mg/mL) were added to the solution. At predetermined time intervals, solution (20 μL each tube) was withdrawn and centrifuged, up-clear solution (10 μL) was stained with Coomassie blue (200 μL), and the absorbance at 595 nm was detected on an Infinite 200 PRO multimode plate reader (Tecan Group Ltd.). The insulin concentration was calibrated by a standard curve.

(6) In Vitro Insulin (or GOx) Release from Ins-NC (or GOx-NC) from the Gel (with Insulin as an Example).

Ins-NC (1 mg/mL) solution and radical initiator were mixed with m-PVA solution (5 wt % in $H_2O$) and irradiated to form a gel. The gel was added to centrifuge tubes containing glucose (100 or 400 mg/dL). At predetermined time intervals, solution (10 μL each tube) was withdrawn, stained with Coomassie blue (200 μL) and the absorbance at 595 nm was detected on an Infinite 200 PRO multimode plate reader (Tecan Group Ltd.). The insulin concentration was calibrated by a standard curve.

(7) Fabrication of Microneedle Array Patch (with MN(G+C+I) as an Example).

All the MNs in this study were fabricated using five uniform silicone molds from Blueacre Technology Ltd. Each MN had a round base of 300 μm in diameter, which tapers over a height of 600 μm to a tip radius of around 5 μm. The MNs were arranged in a 20×20 array with 600 μm tip-tip spacing. First, diluted aqueous solutions of PVA (contain 10% m-PVA, 3.5 wt % in $H_2O$, 500 μL), CAT-NG (1 mg in 400 μL $H_2O$) and a photoinitiator (Irgacure 2959; 5% wt/vol) were prepared and mixed. After deposition of this solution (100 μL) in a silicone mold, the solution was kept under reduced vacuum for 30 minutes and then transferred to a Hettich Universal 32R centrifuge for 30 min at 2000 rpm to compact gel solution into MN cavities to form a membrane on the mold. Then, diluted aqueous solutions of PVA: PVP (2:1), m-PVA (5% in total), GOx-NC, Ins-NC and photoinitiator (Irgacure 2959; 5% wt/vol) were loaded into a mold, and this procedure was repeated for several times until predetermined amount of Ins-NC was loaded. Finally, the microneedle array patch was dried under vacuum for 2 days. After the desiccation, the MN arrays were carefully separated from the silicone mold, and the MNs underwent crosslinking via UV irradiation (wavelength of 365 nm) for a short period. The morphology of the MNs was characterized on an FEI Verios 460L field-emission scanning electron microscope.

(8) The Mechanical Strength Test.

The mechanical strength of microneedles with a stress-strain gauge was determined by pressing a stainless-steel plate against microneedles on an MTS 30G tensile testing machine. The initial gauge was 2.00 mm between the tips of microneedle and the plate, with 10.00 N as the load cell capacity. The speed of the plate approaching microneedles was set as 0.1 mm/s. The failure force of microneedles was recorded as the force at which the needle began to buckle.

(9) In Vivo Studies Using Streptozotocin-Induced Diabetic Mice.

The in vivo efficacy of MN-array patches for diabetes treatment was evaluated in adult diabetic mice (male C57B6, age 8 weeks; Jackson Laboratory) induced using streptozotocin. The animal study protocol was approved by the Institutional Animal Care and Use Committee at North Carolina State University and the University of North Carolina at Chapel Hill. The blood glucose levels were measured using tail vein blood samples (~3 μL) of mice using the Clarity GL2Plus glucose meter (Clarity Diagnostics). The monitor of mouse glucose levels was started two days before drug administration. Five mice from each group were selected to be treated using MN or native insulin. The glucose level of each mouse was monitored until stabilization.

(10) In Vitro Skin Penetration Test.

To evaluate the in vitro skin penetrating ability of MNs, the MNs were inserted into the skin of the mouse for 10 min. The skin was stained with trypan blue for 10 min before imaging by optical microscopy (Leica EZ4 D stereomicroscope).

(11) Statistical Analysis.

Differences in blood glucose levels between the treated groups and controlled groups were determined by unpaired student's t-test. The results were considered statistically significant if the two-tailed P-values were less than 0.05. The statistical approach remained consistent throughout all analyses.

(12) Animal Experiment.

The sample size calculated by power analysis: G*power 3.1. The experiments did not use a method of randomization. The investigators were not blinded to allocation during experiments and outcome assessment.

E. References

A. A. Obaidat, K. Park, *Pharmaceut. Res.* 1996, 13, 989-995.

A. Matsumoto, R. Yoshida, K. Kataoka, *Biomacromolecules* 2004, 5, 1038-1045.

B. W. Bequette, *Diabetes Technol. Ther.* 2005, 7, 28-47.

C. De Duve, P. Baudhuin, *Physiol. Rev.* 1966, 46, 323-357.

C. M. Hassan, F. J. Doyle, N. A. Peppas, *Macromolecules* 1997, 30, 6166-6173.

C. M. Wong, K. H. Wong, X. D. Chen, *Appl. Microbiol. Biotechnol.* 2008, 78, 927-938.

C. R. Gordijo, K. Koulajian, A. J. Shuhendler, L. D. Bonifacio, H. Y. Huang, S. Chiang, G. A. Ozin, A. Giacca, X. Y. Wu, *Adv. Funct. Mater.* 2011, 21, 73-82

C. Wang, Y. Q. Ye, W. J. Sun, J. C. Yu, J. Q. Wang, D. S. Lawrence, J. B. Buse, Z. Gu, *Adv. Mater.* 2017, 29. 1606617.

D. H. Chou, M. J. Webber, B. C. Tang, A. B. Lin, L. S. Thapa, D. Deng, J. V. Truong, A. B. Cortinas, R. Langer, D. G. Anderson, *Proc. Natl. Acad. Sci. U.S.A.* 2015, 112, 2401-2406

D. R. Owens, B. Zinman, G. B. Bolli, *Lancet* 2001, 358, 739-746.

D. Scott, A. Fisher, *J. Pharmacol. Exp. Ther.* 1936, 58, 78-92.

D. Shiino, Y. Murata, A. Kubo, Y. J. Kim, K. Kataoka, Y. Koyama, A. Kikuchi, M. Yokoyama, Y. Sakurai, T. Okano, *J. Control. Release* 1995, 37, 269-276.

E. Cengiz, J. L. Sherr, S. A. Weinzimer, W. V. Tamborlane, *Expert Rev. Med. Devices* 2011, 8, 449-458;

F. Balkwill, *Eur. J. Cancer* 2006, 42, 571-571.

F. Liu, S. C. Song, D. Mix, M. Baudyš, S. W. Kim, *Bioconjug. Chem.* 1997, 8, 664-672

G. Saravanakumar, J. Kim, W. J. Kim, *Advanced Science* 2017, 4, 1600124.

G. Springsteen, B. Wang, *Tetrahedron* 2002, 58, 5291-5300.

I. C. Lee, J.-S. He, M.-T. Tsai, K.-C. Lin, *J. Mater. Chem.* B 2015, 3, 276-285.

J. C. Yu, C. G. Qian, Y. Q. Zhang, Z. Cui, Y. Zhu, Q. D. Shen, F. S. Ligler, J. B. Buse, Z. Gu, *Nano Lett* 2017, 17, 733-739

J. Yu, Y. Zhang, Y. Ye, R. DiSanto, W. Sun, D. Ranson, F. S. Ligler, J. B. Buse, Z. Gu, *Proc. Natl. Acad. Sci.* U S. A. 2015, 112, 8260-8265.

K. Kataoka, H. Miyazaki, M. Bunya, T. Okano, Y. Sakurai, *J. Am. Chem. Soc.* 1998, 120, 12694-12695

K. M. Bratlie, R. L. York, M. A. Invernale, R. Langer, D. G. Anderson, *Adv. Healthc. Mater.* 2012, 1, 267-284

K. Podual, F. J. Doyle Iii, N. A. Peppas, *J. Control. Release* 2000, 67, 9-17.

K. Podual, F. J. Doyle, N. A. Peppas, *Polymer* 2000, 41, 3975-3983.

K. Zhang, X. Y. Wu, *J. Control. Release* 2002, 80, 169-178.

M. Brownlee, A. Cerami, *Diabetes* 1983, 32, 499-504

M. Brownlee, A. Cerami, *Science* 1979, 206, 1190-1191;

M. Piest, X. L. Zhang, J. Trinidad, J. F. J. Engbersen, *Soft Matter* 2011, 7, 11111-11118

M. Piest, X. Zhang, J. Trinidad, J. F. J. Engbersen, *Soft Matter* 2011, 7, 11111-11118.

Matsumoto, T. Kurata, D. Shiino, K. Kataoka, *Macromolecules* 2004, 37, 1502-1510

N. A. Peppas, Y. Huang, M. Torres-Lugo, J. H. Ward, J. Zhang, *Annu. Rev. Biomed. Eng.* 2000, 2, 9-29;

O. Olatunji, D. B. Das, M. J. Garland, L. Belaid, R. F. Donnelly, *J. Pharm. Sci.* 2013, 102, 1209-1221

O. Veiseh, B. C. Tang, K. A. Whitehead, D. G. Anderson, R. Langer, *Nat. Rev. Drug Discov.* 2015, 14, 45-57.

O. Wintersteiner, H. A. Abramson, *J. Biol. Chem.* 1933, 99, 741-753.

R. Mo, T. Jiang, J. Di, W. Tai, Z. Gu, *Chem. Soc. Rev.* 2014, 43, 3595-3629.

R. Mo, T. Jiang, J. Di, W. Tai, Z. Gu, *Chem. Soc. Rev.* 2014, 43, 3595-3629;

S. Joel, K. B. Turner, S. Daunert, *ACS Chem. Biol.* 2014, 9, 1595-1602

S. P. Davis, B. J. Landis, Z. H. Adams, M. G. Allen, M. R. Prausnitz, *J. Biomech.* 2004, 37, W. A. Broom, C. E. Coulthard, M. R. Gurd, M. E. Sharpe, *Br. J. Pharmacol. Chemother.* 1946, 1, 225-233.

W. L. A. Brooks, B. S. Sumerlin, *Chem. Rev.* 2016, 116, 1375-1397.

W. Park, D. Kim, H. C. Kang, Y. H. Bae, K. Na, *Biomaterials* 2012, 33, 8848-8857.

W. Tai, R. Mo, J. Di, V. Subramanian, X. Gu, J. B. Buse, Z. Gu, *Biomacromolecules* 2014, 15, 3495-3502.

X. L. Hu, J. C. Yu, C. G. Qian, Y. Lu, A. R. Kahkoska, Z. G. Xie, X. B. Jing, J. B. Buse, Z. Gu, *ACS Nano* 2017, 11, 613-620.

X. Liu, J. Xiang, D. Zhu, L. Jiang, Z. Zhou, J. Tang, X. Liu, Y. Huang, Y. Shen, *Adv. Mater.* 2016, 28, 1743-1752.

Y. Dong, W. Wang, O. Veiseh, E. A. Appel, K. Xue, M. J. Webber, B. C. Tang, X.-W. Yang, G. C. Weir, R. Langer, D. G. Anderson, *Langmuir* 2016, 32, 8743-8747.

Y. Liu, J. Du, M. Yan, M. Y. Lau, J. Hu, H. Han, O. O. Yang, S. Liang, W. Wei, H. Wang, J. Li, X. Zhu, L. Shi, W. Chen, C. Ji, Y. Lu, *Nat. Nano.* 2013, 8, 187-192.

Y. Ohkubo, H. Kishikawa, E. Araki, T. Miyata, S. Isami, S. Motoyoshi, Y. Kojima, N. Furuyoshi, M. Shichiri, *Diabetes Res. Clin. Pract.* 1995, 28, 103-117;

Y. Yamamoto, H. Koma, T. Yagami, *Neurotoxicology* 2015, 49, 86-93.

Z. Gu, A. A. Aimetti, Q. Wang, T. T. Dang, Y. Zhang, O. Veiseh, H. Cheng, R. S. Langer, D. G. Anderson, *ACS Nano* 2013, 7, 4194-4201;

Z. Gu, T. T. Dang, M. Ma, B. C. Tang, H. Cheng, S. Jiang, Y. Dong, Y. Zhang, D. G. Anderson, *ACS Nano* 2013, 7, 6758-6766;

What is claimed is:

1. A microneedle patch comprising diblock copolymer micelles; wherein the diblock copolymer micelles comprise separately insulin and a glucose responsive enzyme; wherein the diblock copolymer comprises mPEG$_n$-poly(2-(dimethylamino)ethyl methacrylate-4-(bromomethyl)phenylboronic acid)$_m$ of formula 1 shown below:

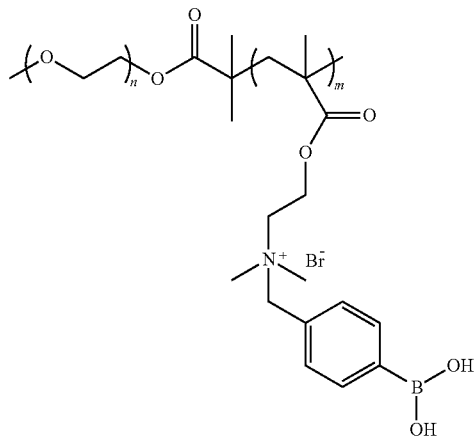

(MPEG$_n$-P(DMAEMA-PBA)$_m$); wherein n can be between 1 and 8,000; and wherein m can be between 1 and 18,000; wherein the microneedles are coated with H$_2$O$_2$ scavenging enzyme; wherein the diblock copolymer micelles further comprise poly(vinyl alcohol) methacrylate (m-PVA); and wherein the insulin dissociates from the micelle in an acidic and oxidative environment.

2. The microneedle patch of claim 1, wherein the glucose responsive enzyme is glucose oxidase.

3. The microneedle patch of claim 1, wherein the H$_2$O$_2$ scavenging enzyme comprises catalase.

4. The microneedle patch of claim 1, wherein the microneedles comprise a core and the diblock copolymer micelles are crosslinked to the microneedle core via non-cleavable covalent bond.

5. A self-regulating insulin delivery system comprising the microneedle patch of claim 1.

6. A method of treating hyperglycemia in a subject comprising administering to the subject the microneedle patch of claim 1.

7. The method of claim 6, wherein the hyperglycemia is a symptom of diabetes.

* * * * *